(12) United States Patent
Nakafuji et al.

(10) Patent No.: US 12,305,131 B1
(45) Date of Patent: May 20, 2025

(54) MODULAR ARTIFICIAL INTELLIGENCE-DRIVEN PLASMA GASIFICATION PROCESS FOR RESOURCE RECOVERY

(71) Applicant: Oceanit Laboratories, Inc., Honolulu, HI (US)

(72) Inventors: Glen Nakafuji, Honolulu, HI (US); Vinod Veedu, Houston, TX (US); Erika Brown, Kailua, HI (US); Ganesh Arumugam, Honolulu, HI (US); Matthew Williams, Honolulu, HI (US); Bryce Davis, Kapolei, HI (US)

(73) Assignee: Oceanit Laboratories, Inc., Honolulu, HI (US)

( * ) Notice: Subject to any disclaimer, the term of this patent is extended or adjusted under 35 U.S.C. 154(b) by 0 days.

(21) Appl. No.: 17/968,406

(22) Filed: Oct. 18, 2022

Related U.S. Application Data

(60) Provisional application No. 63/257,109, filed on Oct. 18, 2021.

(51) Int. Cl.
*C10J 3/18* (2006.01)
*C01B 3/02* (2006.01)
(Continued)

(52) U.S. Cl.
CPC ............... *C10J 3/18* (2013.01); *C01B 3/02* (2013.01); *C01B 5/00* (2013.01); *C01C 1/08* (2013.01);
(Continued)

(58) Field of Classification Search
CPC ....... C10J 3/18; C10J 3/723; C10J 3/82; C10J 2300/00; C10J 2300/1238;
(Continued)

(56) References Cited

U.S. PATENT DOCUMENTS

| 4,453,949 A * | 6/1984 | Fasching ............... C10J 3/42 48/77 |
| 2003/0130360 A1* | 7/2003 | Kindig .................. C07C 1/0425 518/703 |

(Continued)

FOREIGN PATENT DOCUMENTS

WO  WO-2020166659 A1 * 8/2020

OTHER PUBLICATIONS

Machine Translation of WO 2020166659 A1 (Mar. 21, 2024) (Year: 2024).*

*Primary Examiner* — Matthew J Merkling
(74) *Attorney, Agent, or Firm* — Fresh IP PLC; Clifford D. Hyra; Aubrey Y Chen (57) ABSTRACT

Disclosed herein are novel devices, systems, and methods for resource recovery from various feed streams, including both liquid and solid waste streams. Specifically disclosed is a plasma gasification unit and/or system operated or controlled by artificial intelligence (AI). The AI can utilize reinforcement learning (RL) processes to adjust operational parameters for maximizing efficiency and/or output. The plasma gasification unit and/or system may be modular and/or mobile, with portions sized such that they may be contained in one or more shipping containers. The plasma gasification unit and/or system may also include one or more plasma gasification chambers, and uses electrical energy to form a high temperature plasma arc that gasifies feed materials (e.g., brine, brackish water, plastics) into saleable products (e.g., hydrogen, syngas and other fuels, methanol, ammonia, urea).

10 Claims, 6 Drawing Sheets

(51) Int. Cl.
*C01B 5/00* (2006.01)
*C01C 1/08* (2006.01)
*C02F 1/46* (2023.01)
*C07C 29/152* (2006.01)
*C07C 273/10* (2006.01)
*C10J 3/72* (2006.01)
*C10J 3/82* (2006.01)
*H01M 8/0606* (2016.01)

(52) U.S. Cl.
CPC .......... *C02F 1/4608* (2013.01); *C07C 29/152* (2013.01); *C07C 273/10* (2013.01); *C10J 3/723* (2013.01); *C10J 3/82* (2013.01); *H01M 8/0606* (2013.01); *C10J 2200/00* (2013.01); *C10J 2300/1238* (2013.01); *C10J 2300/1665* (2013.01); *C10J 2300/1668* (2013.01); *C10J 2300/1684* (2013.01)

(58) Field of Classification Search
CPC ........ C10J 2300/1665; C10J 2300/1668; C10J 2300/1684; C01B 3/02; C01B 5/00; C01C 1/08; C02F 1/4608; C07C 29/152; C07C 273/10; H01M 8/0606
See application file for complete search history.

(56) References Cited

U.S. PATENT DOCUMENTS

| | | | |
|---|---|---|---|
| 2003/0191196 A1* | 10/2003 | Madhubhai | C01B 3/48 518/704 |
| 2008/0277265 A1* | 11/2008 | Tsangaris | C01B 3/386 204/422 |
| 2010/0319255 A1* | 12/2010 | Struble | C10K 3/001 48/197 R |
| 2011/0201701 A1* | 8/2011 | Lucas | C10J 3/26 422/187 |
| 2012/0058403 A1* | 3/2012 | Edlund | C01B 3/323 422/187 |
| 2013/0012605 A1* | 1/2013 | Zhou | C10J 3/30 422/187 |
| 2013/0104457 A1* | 5/2013 | Jorgenson | C10J 3/005 48/197 R |
| 2013/0252115 A1* | 9/2013 | Hong | F01K 13/00 123/3 |
| 2022/0081629 A1* | 3/2022 | Do | C10J 3/20 |
| 2022/0411264 A1* | 12/2022 | Do | C09C 1/54 |

* cited by examiner

MODULAR ARTIFICIAL INTELLIGENCE-DRIVEN PLASMA GASIFICATION PROCESS FOR RESOURCE RECOVERY

CROSS-REFERENCE TO RELATED APPLICATION

This application claims priority to U.S. Provisional Application No. 63/257,109, filed Oct. 18, 2021, which is hereby incorporated by reference in its entirety.

STATEMENT REGARDING FEDERALLY SPONSORED RESEARCH OR DEVELOPMENT

The invention described herein was made with U.S. government ("Government") support under Contract No. DE-SC0022504, awarded by the U.S. Department of Energy (DOE). As a result, the Government has certain rights in this invention.

FIELD

The application relates generally to devices, systems, and methods relating to plasma gasification. In particular, the application relates to artificial intelligence (AI)-driven plasma gasification that can be optimized for maximum output.

BACKGROUND

Resource recovery is important in many different industries and applications, including, for example, energy generation, waste disposal, recycling, material reuse, and the like. Specifically, enhanced recovery of resources in waste materials and/or waste streams can contribute to less overall waste and increase utilization of such resources.

With respect to energy generation, a great deal of potential energy resources lies in both industrial and public waste streams. Many processes, across a variety of different industries, produce material streams (e.g., waste streams) that must be processed at treatment facilities or otherwise disposed of through sequestration or other means. Recovering resources from these material streams can result in a reduction of waste production and waste treatment, as well as a decreased net usage of fossil fuels, leading to greener energy generation and energy utilization practices. However, resource recovery requires energy-efficient equipment and methods in order to be successful at recovering potential energy resources in a scalable and cost-efficient manner.

Plasma gasification is a thermal process used to convert various organic matter and organic materials into synthetic gas ("syngas"). Such gasification is used in waste treatment in order to convert refuse or biomass waste into potentially useful fuel. However, the current state-of-the-art relies on manual or computer-controlled systems that can be relatively cost-ineffective and fail to optimally recover resources in the waste stream, leading to inefficiencies.

Given the foregoing, there exists a significant need for novel plasma gasification techniques that result in increased output and efficiency, as well as increased operational flexibility.

SUMMARY

It is to be understood that both the following summary and the detailed description are exemplary and explanatory and are intended to provide further explanation of the invention as claimed. Neither the summary nor the description that follows is intended to define or limit the scope of the invention to the particular features mentioned in the summary or in the description.

In certain embodiments, the disclosed embodiments may include one or more of the features described herein.

In at least one embodiment, a plasma gasification system is disclosed. The system may be controlled through artificial intelligence (AI), thereby maximizing resource harvesting and/or recovery of the unit. In at least some embodiments, reinforcement learning (RL) methods and/or algorithms are used. Operational data collected by the plasma gasification system can be combined with operational goals to optimize efficiency, specifically by determining the optimal operational parameters of the gasification unit needed to maximize output. Specifically, the AI, which can include RL, can be applied to one or more control systems of the plasma gasification system to use existing, monitored operational parameters to guide operations of the plasma gasification system, and to adjust the operations and/or control of the plasma gasification system.

In at least a further embodiment, the plasma gasification system may comprise multiple units, some or all of which are mobile and/or modular. Specifically, one or more units may be configured to be sized such that the unit or units may be contained in one or more shipping containers of the type used to ship bulk goods (e.g., Container Express (CONEX) containers that are familiar to those of skill in the art). The unit or units may therefore be transported to various locations (e.g., waste disposal or waste recycling areas) where feed streams, such as, for instance, waste, are located. The unit or units can thus be operated in these locations to recover materials, such as, for instance, organic material, from the feed streams.

In at least an additional embodiment, the plasma gasification system is feed agnostic (i.e., the system is operable to recover energy resources from a variety of feed sources). The system is configured to be operated at a sufficiently high temperature such that the unit is not restricted to specific feed streams or feed materials. The system can therefore harvest resources from a wide variety of feed materials, such as, for example, plastics, solid waste, biological waste, biomass, solid waste, and other material that contains either valuable elements or organic material (e.g., from which energy sources, such as syngas, can be produced).

In at least one example a plasma gasification system is disclosed. The system includes one or more plasma gasification chambers powered by one or more electricity sources, each of the one or more plasma gasification chambers including a power inlet for inputting electricity from the one or more electricity sources, a gas inlet for inputting one or more gases (e.g., nitrogen, argon, and/or other gases), and an arc plasma gasifier connected to both the power inlet and the gas inlet, one or more feed inlets connected from one or more feed streams to the one or more plasma gasification chambers; a power storage unit, a product gas storage unit, and one or more product outlets connected from the one or more plasma gasification chambers to at least one of the power storage unit and the product gas storage unit. The one or more plasma gasification chambers (i) use the electricity to form a high-temperature plasma arc to gasify one or more feed materials from one or more feed streams into one or more products, and (ii) transfer the one or more products via the one or more product outlets, from the one or more plasma gasification chambers to at least one of the power storage unit and the product gas storage unit.

In an example, the electricity is provided by a source selected from the group consisting of a geothermal source, a fossil fuel source, a biomass source, a solar source, a renewable energy source, and combinations thereof.

In example, the one or more feed materials are selected from the group consisting of: liquid waste, solid waste, brine, sea water, salt water, brackish water, produced water, waste water, plastics, biomass, biological waste, and combinations thereof.

In another example, the one or more products are selected from the group consisting of: repurposed water, hydrogen gas, syngas, fuel, electricity, methanol, ammonia, urea, and combinations thereof.

In an example, the plasma gasification system includes one or more artificial intelligence (AI) systems. The one or more AI systems can be configured to collect data from operation of the one or more plasma gasification chambers, and use the data to optimize one or more operation parameters of the one or more plasma gasification chambers to increase output of the one or more products.

In an example, the one or more plasma gasification chambers are configured to operate in batch mode to process the one or more feed materials under one or more operating conditions, and wherein the one or more AI systems are configured to optimize the one or more operating conditions to maximize production of the one or more products while minimizing waste products.

The aforementioned one or more AI systems may additionally include one or more AI controllers that incorporate reinforcement learning (RL) to optimize, based on one or more user-provided operational goals, one or more operation parameters of the one or more plasma gasification chambers. Additionally, the one or more AI systems can be configured to utilize monitored operational parameters of the plasma gasification system to guide operation of the plasma gasification system and to adjust control of the plasma gasification system.

In an example, a plasma gasification system includes one or more plasma gasification chambers, the one or more plasma gasification chambers including one or more arc plasma gasifiers. The one or more plasma gasification chambers are configured to convert one or more feed materials into one or more products by performing: a gasification process, a gas separation process, and a product separation process. The one or more products can include one or more gases.

In an example, the aforementioned gasification process includes inputting one or more feed materials into the one or more arc plasma gasifiers, and generating, by the one or more arc plasma gasifiers, a gas mixture from the one or more feed materials.

In an example, the gas separation process includes separating the gas mixture into one or more constituent gases.

In an example the product separation process includes processing the one or more constituent gases to generate the one or more products.

In an example, the one or more constituent gases include hydrogen gas, and the processing the one or more constituent gases further includes feeding the hydrogen gas into a fuel cell to generate electricity and purified water.

In an example, the one or more constituent gases include at least one of: carbon monoxide and carbon dioxide, and the processing the one or more constituent gases further comprises at least one of: producing methanol by methanol synthesis, and converting carbon monoxide and water into carbon dioxide and hydrogen gas.

In an example, a plasma gasification method is disclosed. The method includes inputting one or more feed materials, gas (e.g., nitrogen, argon, and/or other gases), and electricity into an arc plasma gasifier, generating, by the arc plasma gasifier, a gas mixture from one or more feed materials, separating the gas mixture into one or more constituent gases, and processing the one or more constituent gases to generate one or more products.

In an example, the one or more products include stored hydrogen gas, generated electricity, and purified water, the one or more constituent gases include hydrogen gas, and the processing the one or more constituent gases further includes storing at least a portion of the hydrogen gas in a hydrogen storage unit to generate the stored hydrogen gas, and feeding at least another portion of the hydrogen gas into a fuel cell to generate the generated electricity and the purified water.

In an example, the one or more products include methanol, the one or more constituent gases include at least one of carbon monoxide and carbon dioxide, and the processing the one or more constituent gases further includes synthesizing the methanol from at least one of the carbon monoxide and the carbon dioxide.

In an example the method includes converting at least a portion of flue gas from the arc plasma gasifier into methanol.

In an example, the method includes converting at least another portion of the flue gas into ammonia.

In an example, the method includes converting at least a portion of the ammonia into urea.

These and further and other objects and features of the invention are apparent in the disclosure, which includes the above and ongoing written specification, as well as the drawings.

BRIEF DESCRIPTION OF THE DRAWINGS

The accompanying drawings, which are incorporated herein and form a part of the specification, illustrate exemplary embodiments and, together with the description, further serve to enable a person skilled in the pertinent art to make and use these embodiments and others that will be apparent to those skilled in the art. The invention will be more particularly described in conjunction with the following drawings wherein.

DETAILED DESCRIPTION

The present invention is more fully described below with reference to the accompanying figures. The following description is exemplary in that several embodiments are described (e.g., by use of the terms "preferably," "for example," or "in one embodiment"); however, such should not be viewed as limiting or as setting forth the only embodiments of the present invention, as the invention encompasses other embodiments not specifically recited in this description, including alternatives, modifications, and equivalents within the spirit and scope of the invention. Further, the use of the terms "invention," "present invention," "embodiment," and similar terms throughout the description are used broadly and not intended to mean that the invention requires, or is limited to, any particular aspect being described or that such description is the only manner in which the invention may be made or used. Additionally, the invention may be described in the context of specific applications; however, the invention may be used in a variety of applications not specifically described.

The embodiment(s) described, and references in the specification to "one embodiment", "an embodiment", "an example embodiment", etc., indicate that the embodiment(s) described may include a particular feature, structure, or characteristic. Such phrases are not necessarily referring to the same embodiment. When a particular feature, structure, or characteristic is described in connection with an embodiment, persons skilled in the art may effect such feature, structure, or characteristic in connection with other embodiments whether or not explicitly described.

In the several figures, like reference numerals may be used for like elements having like functions even in different drawings. The embodiments described, and their detailed construction and elements, are merely provided to assist in a comprehensive understanding of the invention. Thus, it is apparent that the present invention can be carried out in a variety of ways, and does not require any of the specific features described herein. Also, well-known functions or constructions are not described in detail since they would obscure the invention with unnecessary detail. Any signal arrows in the drawings/figures should be considered only as exemplary, and not limiting, unless otherwise specifically noted. Further, the description is not to be taken in a limiting sense, but is made merely for the purpose of illustrating the general principles of the invention, since the scope of the invention is best defined by the appended claims.

It will be understood that, although the terms "first," "second," etc. may be used herein to describe various elements, these elements should not be limited by these terms. These terms are only used to distinguish one element from another. Purely as a non-limiting example, a first element could be termed a second element, and, similarly, a second element could be termed a first element, without departing from the scope of example embodiments. As used herein, the term "and/or" includes any and all combinations of one or more of the associated listed items. As used herein, the singular forms "a", "an," and "the" are intended to include the plural forms as well, unless the context clearly indicates otherwise. It should also be noted that, in some alternative implementations, the functions and/or acts noted may occur out of the order as represented in at least one of the several figures. Purely as a non-limiting example, two figures shown in succession may in fact be executed substantially concurrently or may sometimes be executed in the reverse order, depending upon the functionality and/or acts described or depicted.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Conditional language, such as, among others, "can," "could," "might," or "may," unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment.

In general, the word "instructions," as used herein, refers to logic embodied in hardware or firmware, or to a collection of software units, possibly having entry and exit points, written in a programming language, such as, but not limited to, Python, R, Rust, Go, SWIFT, Objective-C, Java, JavaScript, Lua, C, C++, or C#. A software unit may be compiled and linked into an executable program, installed in a dynamic link library, or may be written in an interpreted programming language such as, but not limited to, Python, R, Ruby, JavaScript, or Perl. It will be appreciated that software units may be callable from other units or from themselves, and/or may be invoked in response to detected events or interrupts. Software units configured for execution on computing devices by their hardware processor(s) may be provided on a computer readable medium, such as a compact disc, digital video disc, flash drive, magnetic disc, or any other tangible medium, or as a digital download (and may be originally stored in a compressed or installable format that requires installation, decompression or decryption prior to execution). Such software code may be stored, partially or fully, on a memory device of the executing computing device, for execution by the computing device. Software instructions may be embedded in firmware, such as an EPROM. It will be further appreciated that hardware modules may be comprised of connected logic units, such as gates and flip-flops, and/or may be comprised of programmable units, such as programmable gate arrays or processors. Generally, the instructions described herein refer to logical modules that may be combined with other modules or divided into sub-modules despite their physical organization or storage. As used herein, the term "computer" is used in accordance with the full breadth of the term as understood by persons of ordinary skill in the art and includes, without limitation, desktop computers, laptop computers, tablets, servers, mainframe computers, smartphones, handheld computing devices, and the like.

In this disclosure, references are made to users performing certain steps or carrying out certain actions with their client computing devices/platforms. In general, such users and their computing devices are conceptually interchangeable. Therefore, it is to be understood that where an action is shown or described as being performed by a user, in various implementations and/or circumstances the action may be performed entirely by the user's computing device or by the user, using their computing device to a greater or lesser extent (e.g. a user may type out a response or input an action, or may choose from preselected responses or actions generated by the computing device). Similarly, where an action is shown or described as being carried out by a computing device, the action may be performed autonomously by that computing device or with more or less user input, in various circumstances and implementations.

In this disclosure, various implementations of a computer system architecture are possible, including, for instance, thin client (computing device for display and data entry) with fat server (cloud for app software, processing, and database), fat client (app software, processing, and display) with thin server (database), edge-fog-cloud computing, and other possible architectural implementations known in the art.

Generally, embodiments of the present disclosure are directed towards novel devices, systems, and methods for plasma gasification and, in particular, optimization of plasma gasification processes. Specifically, embodiments are directed towards a plasma gasification unit or system that is operated and/or controlled through artificial intelligence (AI), thereby optimizing output of the plasma gasification. The plasma gasification unit and/or system comprises one or more plasma gasification chambers, and uses electrical energy to form a high temperature plasma arc that gasifies various feed materials (including, but not limited to, plastics, organic waste, and the like) into product gases (including, but not limited to, syngas). A skilled artisan will appreciate that these product gases can be separated into value-added products that can be reused to provide energy.

A plasma gasification system includes one or more plasma gasification chambers powered by one or more electricity sources, one or more feed inlets connected from one or more feed streams to the one or more plasma gasification chambers, a power storage unit, a product gas storage unit, and one or more product outlets connected from the one or more plasma gasification chambers to at least one of: the power storage unit and the product gas storage unit. Each of the one or more plasma gasification chambers further includes a power inlet for inputting electricity from the one or more electricity sources, a gas inlet for inputting one or more gases (e.g., nitrogen, argon, and/or other gases), and an arc plasma gasifier connected to both the power inlet and the gas inlet. The aforementioned one or more plasma gasification chambers (i) use the electricity to form a high-temperature plasma arc to gasify one or more feed materials from one or more feed streams into one or more products, and (ii) transfer the one or more products via the one or more product outlets, from the one or more plasma gasification chambers to at least one of the power storage unit and the product gas storage unit.

In an example, the plasma gasification unit and/or system is modular and/or mobile in nature. The unit and/or system can be separated into one or more portions, or otherwise sized, such that the one or more portions can be transported and reassembled. In a non-limiting example, the plasma gasification unit comprises a plurality of portions such that the unit, or, at minimum, at least some of the plurality of portions, fits within one or more shipping containers (e.g., CONEX containers known in the art).

It should be appreciated that the mobile and/or modular nature of the gasification unit enables easy scalability and operational flexibility since the unit is configured to service different locations easily. Thus, the gasification unit can be transported to different locations where feed streams can be fed into the unit so that the unit can convert feed material (e.g., organic waste) into value-added products (e.g., syngas). Specifically, in a non-limiting embodiment, the plasma gasification unit is used for the production of hydrogen, and can be moved to waste storage locations in which plastics and other waste can be used as feed material to be gasified to produce hydrogen.

In another example, the plasma gasification unit and/or system operates at a high temperature such that it can convert a plurality of feed materials (e.g., plastics, solid waste, biomass, etc.) into valuable and/or resalable products (e.g., syngas). A skilled artisan will appreciate that such a gasification unit can be used to gasify a wide variety of feed streams and is therefore not limited by the type of waste or other feed material the unit can convert into product gases.

As a non-limiting example, the plasma gasification unit and/or system is configured to reduce and convert a variety of waste streams (including, but not limited to, both liquid waste and solid waste) into reusable end products, including, but not limited to, hydrogen, a zero-carbon fuel and that is broadly adaptable for energy use. The unit and/or system may be, in at least one embodiment, a water-energy recovery system that uses arc plasma technology to provide the operational flexibility to dissociate a variety of waste streams into valuable end products, such as, for instance, hydrogen, ammonium, phosphorus, electricity, and repurposed water.

The plasma gasification unit/and or system may be controlled by AI and, in at least one embodiment, by a type of machine learning known in the art as reinforcement learning (RL). The AI/RL controls are configured to control the gasification unit by relying on operational data collected and/or stored by the unit, and by optimization goals input by a user. By combining these sources of data, the AI determines the operational parameters of the unit such that maximum output is achieved. The AI/RL controls may further be configured to utilize existing, monitored operational parameters to guide operation of the plasma gasification unit and/or system and to adjust operation and/or control of the plasma gasification unit and/or system. The plasma gasification unit may further comprise a plurality of diagnostic sensors and/or devices that serve as information feeds to the AI/RL controls that monitor and adjust the operation parameters of the unit.

One of skill in the art will appreciate that the plasma gasification unit described herein enables cost-effective recovery of resources from waste materials and feed streams because the unit can be optimized by, for instance, AI and/or RL controls that automatically set the unit's operational parameters. Such AI/RL controls can also respond faster than a human operator or user to adjust operation of the gasification unit in response to different situations (e.g., a change from one type of raw material input to another, etc.). It should be appreciated that such an optimized gasification unit enables the recycling and reuse of waste streams into energy, thereby resulting in less net waste production and increasing the generation of valuable end products (e.g., greener forms of energy such as hydrogen, repurposed water, etc.).

It should further be appreciated that the gasification unit is modular and/or mobile, thereby enabling greater operational flexibility as compared to fixed gasification units or systems that cannot be transported. A modular and/or mobile gasification unit can be transported to different physical locations that may have different feed streams, resulting in increased resource recovery and greater resource output.

Figure 1:
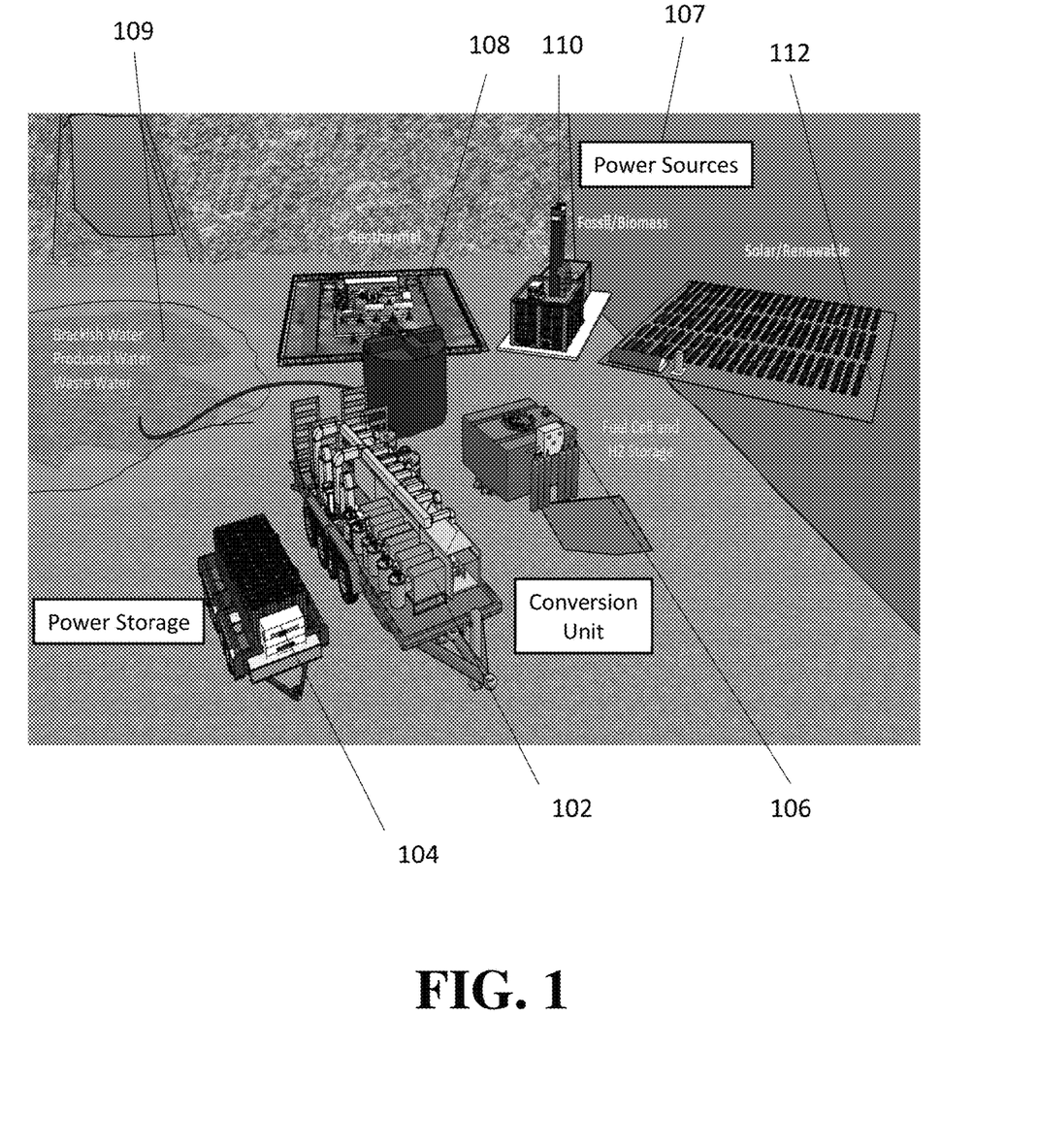
FIG. 1 is a schematic diagram of a plasma gasification system, according to at least one embodiment of the present disclosure.

Turning now to FIG. 1, a plasma gasification system is shown, including a conversion unit 102, a power storage unit 104, and a fuel cell and hydrogen storage unit 106. One or more units of the plasma gasification system are powered by one or more power sources 107, such as, for example, geothermal power source 108, fossil fuel and/or biomass power source 110, and solar and/or renewable power source 112. The conversion unit 102 intakes a feed stream 109, which can be, for instance, brackish water, produced water, and/or waste water. The conversion unit 102 is configured to produce one or more products that can be stored and/or sold, such as electricity (stored in the power storage 104) and hydrogen (stored in the fuel cell and hydrogen storage unit 106). The processes that occur in order to convert an input feed stream into products such as hydrogen are set forth in further detail with respect to FIG. 2.

In at least one embodiment, a plasma gasification unit and/or system (which can include, for instance, the conversion unit 102 shown in FIG. 1) utilizes arc plasma technology and AI/RL to efficiently reduce waste streams (e.g., brine, sea water, brackish water and/or waste water, solid wastes such as plastics) and provide energy recovery simultaneously. Various feed streams, such as, for instance, feed stream 108, can be fed directly into the plasma gasification unit and/or system without the need to pretreat the feed streams. The plasma arc technology converts electricity into very high temperature electric discharges that thermally and chemically break down waste streams very rapidly. A variety of electricity sources can be used as an input, including, but not limited to, fossil fuels, biomass, geothermal, solar, wind, reusable energy, etc. Accordingly, the plasma gasification unit and/or system enables the reduction of waste streams into recoverable components, including, for example, hydrogen, syngas, ammonia, water, and the like. A skilled artisan will appreciate that that the hydrogen and/or syngas can further be utilized as a fuel for energy generation by applying re-engineered fuel cells (such as, for instance, the fuel cell and hydrogen storage 106) or chemical byproducts.

The plasma gasification unit and/or system may comprise a 50 kW plasma torch and gasifier vessel for reducing metered units of feed into increments of syngas for assay and separation into hydrogen and other potential usable products. The vessel may be configured to operate in batch mode, which enables evaluation and/or usage of different feed stream mixtures and operating conditions. Such conditions can be optimized (e.g., by the AI/RL controls) to maximize hydrogen production while minimizing any solid or gaseous waste products. The vessel may further be configured to collect data that can be fed to the AI so that the AI may use the data to guide future operation and optimization of the gasification unit and/or system.

In at least one embodiment, the plasma gasification unit/ and or system comprises one or more AI-driven controls that utilize RL. RL enables the design of an AI controller that optimizes the performance of the gasification unit and/or system given a user-defined cost/reward function. RL further adjusts and optimizes its performance using data obtained from the gasification unit and/or system, thereby correcting for imperfect or absent models of the system dynamics. Accordingly, the plasma gasification unit and/or system can be optimized to maximize output performance parameters, such as, for instance, syngas production and subsequent hydrogen recovery.

In at least a further embodiment, one or more surfaces of the plasma gasification unit and/or system may be coated with surface treatments or coatings that reduce corrosion of parts, reduce the presence of biofouling, and improve flow of materials (e.g., the feed stream) through the unit and/or system. Non-limiting examples of such coatings include nano-composite surface treatments and low-friction omniphobic surface treatments.

Figure 2A:
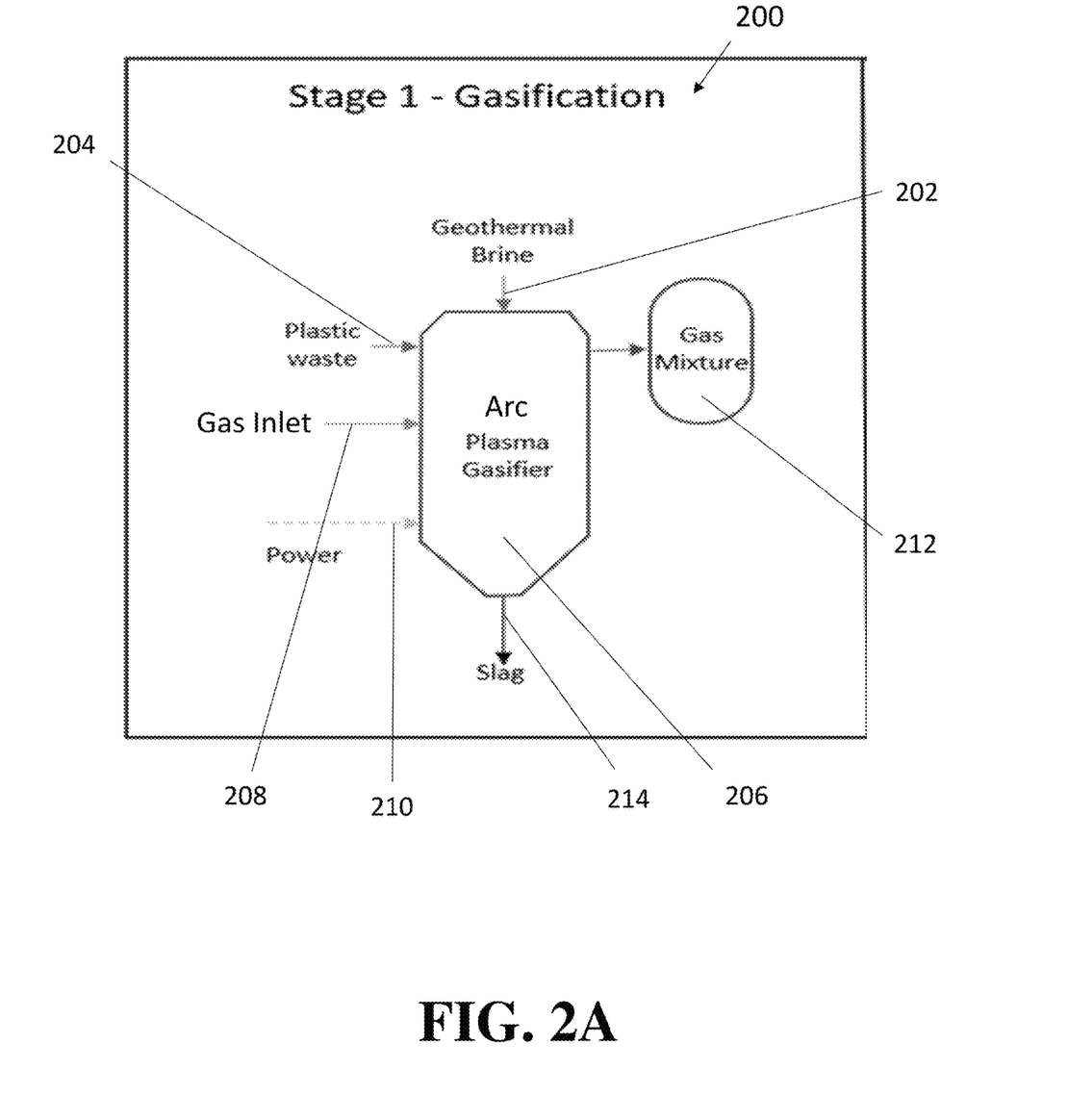
FIGS. 2A-2C are schematic diagrams that illustrate a gasification process (FIG. 2A), a gas separation process (FIG. 2B), and a product generation process (FIG. 2C), according to at least one embodiment of the present disclosure.
Figure 2B:
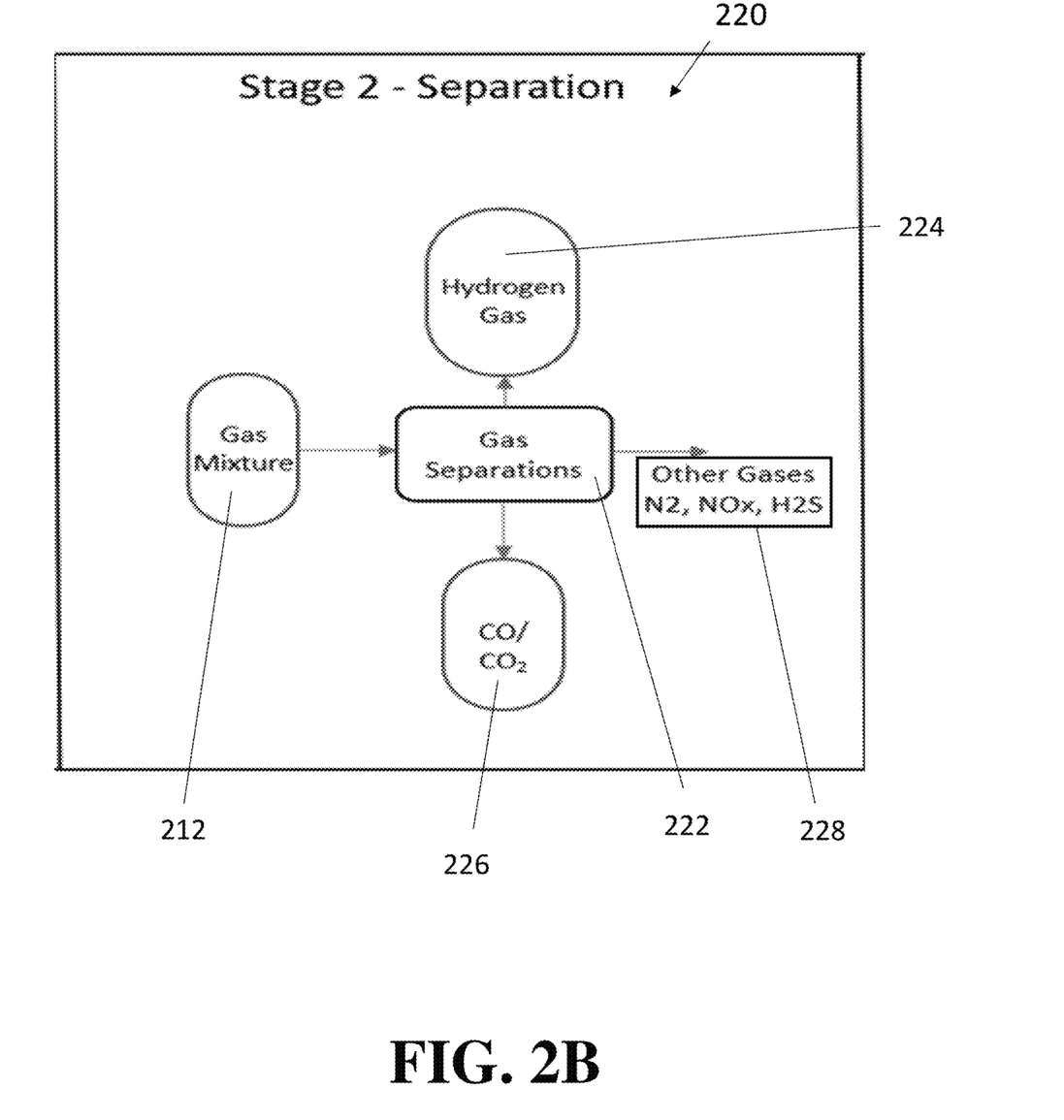
Figure 2C:
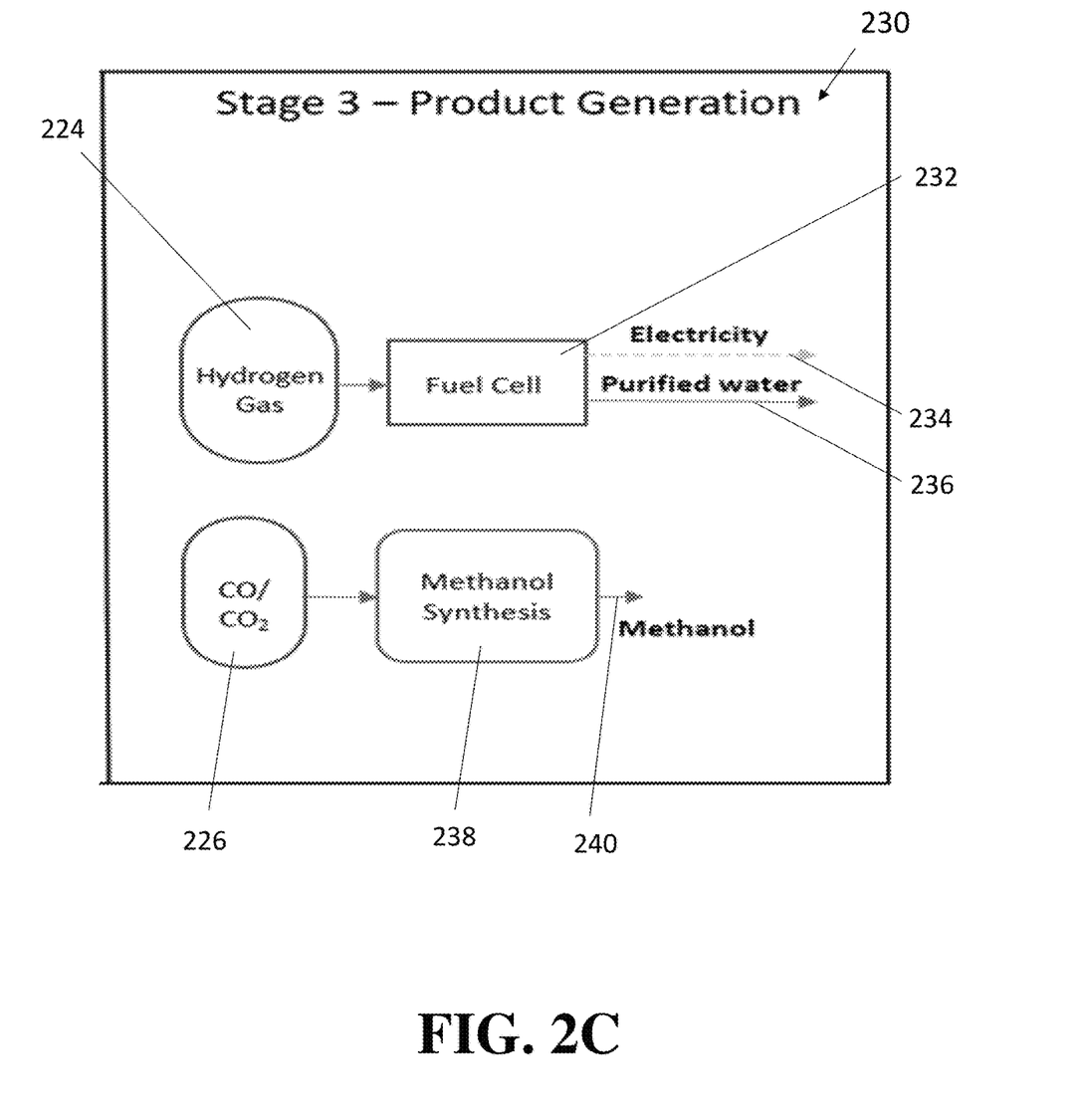

At least one of the plasma gasification units and/or systems mentioned above herein may utilize one or more of the following processes shown in FIGS. 2A-2C for resource recovery. Turning now to FIG. 2A, a gasification process 200 is shown in which one or more feed streams (e.g., geothermal brine 202 and/or plastic waste 204) enter an arc plasma gasifier 206. One or more gases (e.g., nitrogen, argon, and/or other gases) enter via gas inlet 208 and electricity/power 210 also enters the arc plasma gasifier 206. A gas mixture 212 is produced, while slag 214 exits as a waste product.

The gas mixture 212 then undergoes a gas separation process 220, shown in FIG. 2B. The gas mixture 212 is separated via one or more gas separation methods 222 into various constituent gases, including, for example, hydrogen gas 224, carbon monoxide (CO) and/or carbon dioxide ($CO_2$) 226, and/or other additional gases 228 (e.g., nitrogen gas ($N_2$), nitrogen oxides ($NO_x$), hydrogen sulfide ($H_2S$)).

FIG. 2C illustrates a product generation process 230, in which one or more of the constituent gases from the gas separation process 220 undergo further processing to generate products. For instance, the hydrogen gas 224 can be fed into a fuel cell 232, resulting in generation of electricity 234 and purified water 236. Additionally, the CO and/or $CO_2$ 226 can be utilized in a methanol synthesis process 238 to produce methanol 240. A skilled artisan will appreciate that CO and water can also be converted to $CO_2$ and $H_2$ (reaction not shown). Conversion of CO-rich syngas to $CO_2$ and $H_2$ can be achieved by using a commercial water gas shift reaction catalyst. The end product from the water gas shift reaction will result in high hydrogen content and will also convert CO to $CO_2$. Both hydrogen and carbon dioxide may be captured by pressure swing adsorption (PSA) columns with variable adsorbents. Hydrogen produced by the product generation process 230 can be compressed for storage or used directly with operating fuel cells (e.g., the fuel cell 232) for power generation (e.g., generating electricity 234). The operating conditions that result in optimum generation of hydrogen can be found and set by the AI/RL controlling the plasma gasification unit and/or system.

With the high CO content in the flue gas resulting from the arc plasma gasifier 206, syngas can be directly converted to methanol via methanol synthesis 238. One common approach for producing methanol is to use a low-pressure catalytic reaction of syngas. The low pressure allows for operating conditions which favor the conversion of methanol and nearly completely inhibit the production of by-products with high selectivity (>99%). The most common catalyst used in low-pressure methanol production is a Copper-Zinc Oxide catalyst with Aluminum Oxide or Chromium(III) Oxide ($Cu—ZnO—Al_2O_3/Cu—ZnO—Cr_2O_3$). It should be appreciated that the methanol produced (e.g., methanol 240) can be transported or converted into dimethyl ether. A number of commercial large-scale catalyst reactors are available that can be readily integrated to efficiently capture flue gas and hydrogen.

Additionally, syngas could be converted into ammonia, which could then be used as a hydrogen storage material or further modified into urea, which can be stored and shipped. A skilled artisan will appreciate that both ammonia and urea are important and commercially valuable fertilizer chemicals. Ammonia can be produced by reacting hydrogen from the syngas processing (e.g., hydrogen gas 224) with pure nitrogen to form ammonia in a high pressure, high temperature catalyst reaction. The formed ammonia can be shipped and/or stored, or further reacted with the $CO_2$ separated from the syngas (e.g., using PSA) to produce urea.

Thus, one ideal outcome for the plasma gasification units/and or systems described herein are the generation of a pure hydrogen stream for energy use, the conversion of the CO and hydrogen streams into methanol for fuel uses, and/or synthesis of ammonia and/or urea from a nitrogen stream.

One of skill in the art will recognize that embodiments of the disclosure are improvements upon current, state-of-the-art technologies for purifying and/or recycling waste water in particular, including, for instance, electrolysis systems, reverse osmosis systems, nano-filtration systems, and ultraviolet (UV) light filtration systems. Specifically, embodiments of the disclosure do not require any pre-treatment of the feed stream and can utilize a variety of different feed sources (including both solid and liquid feed streams). By contrast, an electrolysis system requires desalination of a brine input stream to reduce degradation of the system. Moreover, various embodiments of the disclosure are modular and/or mobile, meaning they can both be readily moved from site to site and installed quickly on a given site. However, electrolysis systems and other standard desalination and/or filtration systems require a high capital expenditure cost to construct and employ at scale.

Indeed, in a non-limiting example, the plasma gasification system can be used to recover resources from a brine input stream. Unlike standard electrolysis systems, which must incorporate a desalination process prior to hydrogen extraction in order to reduce the effect of salts on the electrolysis system, the plasma gasification system does not require a desalination plant to generate feed water for the steam injection into a plasma gasification chamber. This also enables the plasma gasification system to accommodate, and recover resources from, a variety of feed streams (e.g., biological waste, biomass, brine, plastic waste, coal, etc.).

Figure 3:
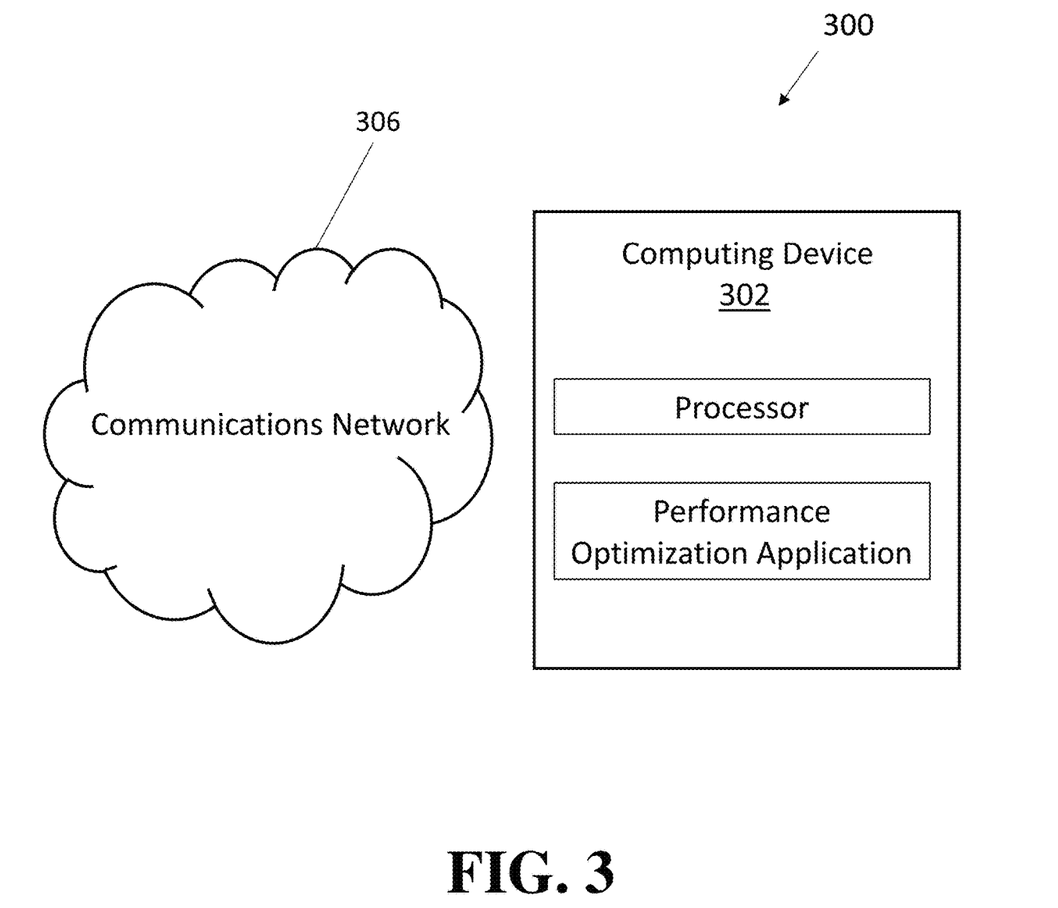
FIG. 3 is a block diagram of a computing system for monitoring, controlling, and/or optimizing a plasma gasification unit and/or system, according to at least one embodiment of the present disclosure.

Turning now to FIG. 3, a block diagram is shown of a computing system 300 for controlling and optimizing a plasma gasification unit and/or system, or one or more parameters thereof, according to an example embodiment. Thus, the computing system 300 may control, for instance, the conversion unit 102 shown in FIG. 1. As mentioned above herein, the computing system may include one or more AI-driven controls that utilize RL in order to maximize output performance parameters of the plasma gasification unit and/or system, such as, for example, syngas production and subsequent hydrogen recovery.

The system 300 comprises one or more computing devices 302 that may execute one or more applications to monitor, control, and/or optimize performance of the plasma gasification unit and/or system. Such applications may be driven, in whole or in part, by AI/RL. Additionally, the applications can be used to send information to, or receive information from, the plasma gasification unit and/or system. The applications can further be capable of scheduled or triggered communications or commands when various events occur (e.g., output of the gasification unit falling below predetermined or pre-set parameters).

The one or more computing devices 302 can be used to store acquired image and computational data, as well as other data in memory and/or a database. The memory may be communicatively coupled to one or more hardware processing devices which are capable of AI/RL.

The one or more computing devices 302 may further be connected to a communications network 304, which can be the Internet, an intranet, or another wired or wireless communication network. For example, the communication network 304 may include a Mobile Communications (GSM) network, a code division multiple access (CDMA) network, 3rd Generation Partnership Project (GPP) network, an Internet Protocol (IP) network, a wireless application protocol (WAP) network, a Wi-Fi network, a satellite communications network, or an IEEE 802.11 standards network, as well as various communications thereof. Other conventional and/or later developed wired and wireless networks may also be used.

The one or more computing devices 302 include at least one processor to process data and memory to store data. The processor processes communications, builds communications, retrieves data from memory, and stores data to memory. The processor and the memory are hardware. The memory may include volatile and/or non-volatile memory, e.g., a computer-readable storage medium such as a cache, random access memory (RAM), read only memory (ROM), flash memory, or other memory to store data and/or computer-readable executable instructions such as a portion or component of the object imaging and detection application. In addition, the one or more computing devices 302 further include at least one communications interface to transmit and receive communications, messages, and/or signals.

Thus, information processed by the one or more computing devices 302, or the applications executed thereon, may be sent to another computing device, such as a remote computing device, via the communication network 306.

Figure 4:
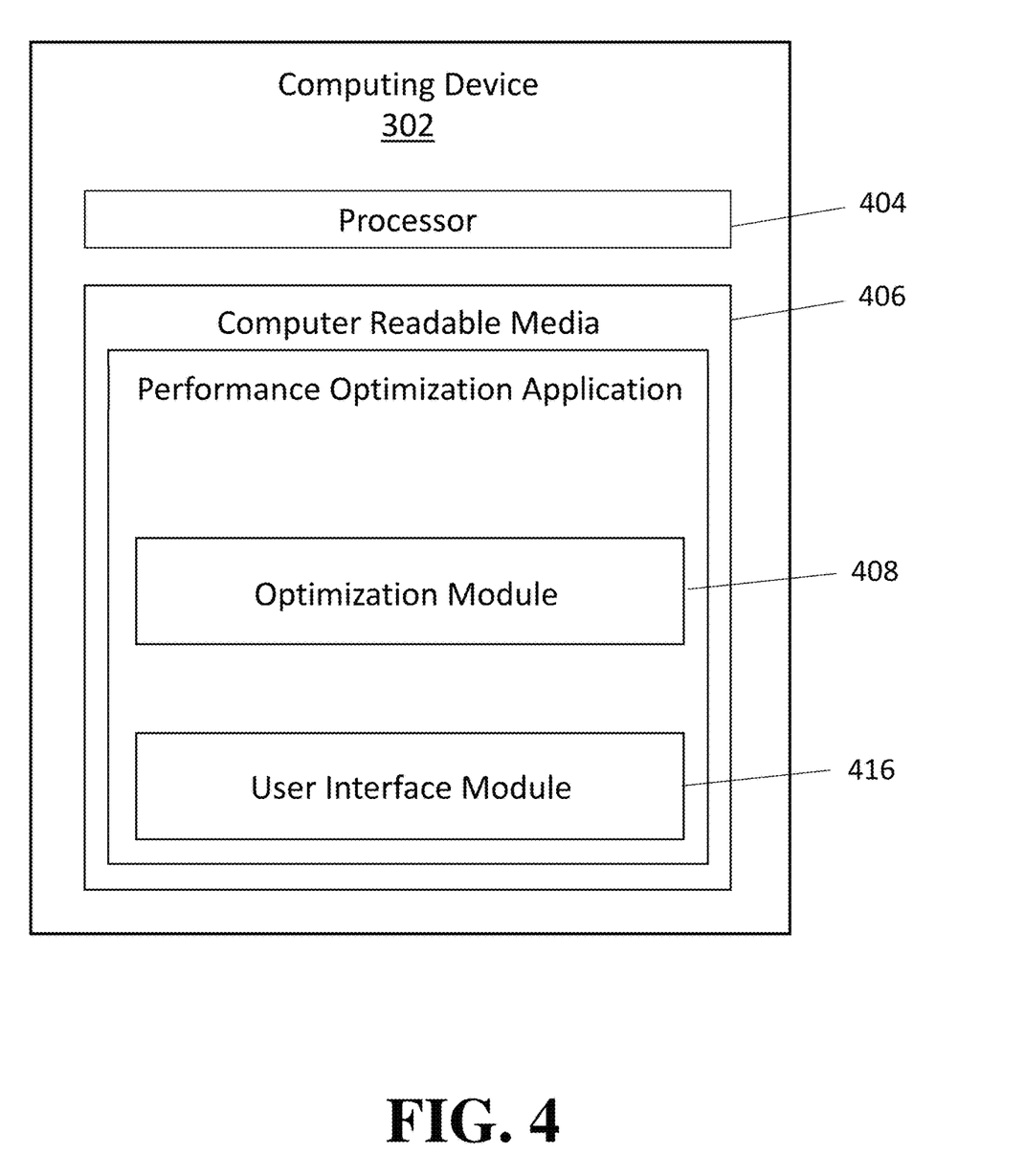
FIG. 4 is a block diagram of a computing device, according to at least one embodiment of the present disclosure.

FIG. 4 illustrates a block diagram of a computing device 302 according to an example embodiment. The computing device 302 includes computer readable media (CRM) 404 in memory on which a performance optimization application 406 or other user interface or application is stored. The computer readable media may include volatile media, non-volatile media, removable media, non-removable media, and/or another available medium that can be accessed by the processor 402. By way of example and not limitation, the computer readable media comprises computer storage media and communication media. Computer storage media includes non-transitory storage memory, volatile media, nonvolatile media, removable media, and/or non-removable media implemented in a method or technology for storage of information, such as computer/machine-readable/executable instructions, data structures, program modules, or other data. Communication media may embody computer/machine-readable/executable instructions, data structures, program modules, or other data and include an information delivery media or system, both of which are hardware.

As stated above herein, such performance optimization application 406 includes an optimization module 408 that is operable to monitor, control, and/or optimize performance of a plasma gasification unit and/or system, and may be driven, in whole or in part, by AI/RL. The performance optimization application 406 may also be operable to obtain data from gasification unit and/or system, and to process that data to correct for imperfect, inaccurate, or absent models regarding the dynamics or operation of the gasification unit.

Using a local high-speed network, the computing device 302 may receive the aforementioned data in near real time from the plasma gasification unit or sensors disposed thereon or therein, process the data, and generate calculations on optimization of one or more parameters. These calculations may be executed by one or more algorithms within the performance optimization application 406 or other stored applications.

Measured or calculated data may be monitored to generate an event and an alert if something is out of range (e.g., one or more operating or performance parameters of the plasma gasification unit and/or system, one or more outputs of the gasification unit, etc.). Such alerts may be sent in real-time or near real-time using an existing uplink or dedicated link. The alerts may be sent using email, SMS, push notification, or using an online messaging platform to end users and computing devices, among others.

The performance optimization application 406 may provide data visualization using a user interface module 416 for displaying a user interface on a display device. As an example, the user interface module 416 generates a native and/or web-based graphical user interface (GUI) that accepts input and provides output viewed by users of the computing device 302. The computing device 302 may provide real-time automatically and dynamically refreshed information on the functioning of the plasma gasification unit and/or system. The user interface module 416 may send data to other modules of the performance optimization application 406 of the computing device 302, and retrieve data from other modules of the performance optimization application of the computing device 302 asynchronously without interfering with the display and behavior of the user interface displayed by the computing device 302.

These and other objectives and features of the invention are apparent in the disclosure, which includes the above and ongoing written specification.

The foregoing description details certain embodiments of the invention. It will be appreciated, however, that no matter how detailed the foregoing appears in text, the invention can be practiced in many ways. As is also stated above, it should be noted that the use of particular terminology when describing certain features or aspects of the invention should not be taken to imply that the terminology is being re-defined herein to be restricted to including any specific characteristics of the features or aspects of the invention with which that terminology is associated.

The invention is not limited to the particular embodiments illustrated in the drawings and described above in detail. Those skilled in the art will recognize that other arrangements could be devised. The invention encompasses every possible combination of the various features of each embodiment disclosed. One or more of the elements described herein with respect to various embodiments can be implemented in a more separated or integrated manner than explicitly described, or even removed or rendered as inoperable in certain cases, as is useful in accordance with a particular application. While the invention has been described with reference to specific illustrative embodiments, modifications and variations of the invention may be constructed without departing from the spirit and scope of the invention as set forth in the following claims.

We claim:

1. A plasma gasification method comprising:
   inputting one or more feed materials, one or more gases, and electricity into an arc plasma gasifier;
   generating, by the arc plasma gasifier, a gas mixture from the one or more feed materials, the one or more gases, and the electricity;
   separating at least one constituent gas of the gas mixture from one or more other constituent gases of the gas mixture; and
   processing the at least one constituent gas to generate one or more products,
   wherein the one or more feed materials comprises a liquid feed stream of geothermal brine.

2. The plasma gasification method of claim 1, wherein the one or more products comprise a plurality of products, wherein the plurality of products comprise stored hydrogen gas, generated electricity, and purified water, wherein the at least one constituent gas comprises hydrogen gas, and wherein the processing the at least one constituent gas further comprises:
   storing at least a portion of the hydrogen gas in a hydrogen storage unit to generate the stored hydrogen gas; and
   feeding at least another portion of the hydrogen gas into a fuel cell to generate the generated electricity and the purified water.

3. The plasma gasification method of claim 1, wherein the one or more products comprise methanol, wherein the at least one constituent gas comprises at least one of: carbon monoxide and carbon dioxide, and wherein the processing the at least one constituent gas further comprises:
   synthesizing the methanol from at least one of the carbon monoxide and the carbon dioxide.

4. The plasma gasification method of claim 1, further comprising:
   converting at least a portion of flue gas from the arc plasma gasifier into methanol.

5. The plasma gasification method of claim 4, further comprising:
   converting at least another portion of the flue gas into ammonia.

6. The plasma gasification method of claim 5, further comprising:
   converting at least a portion of the ammonia into urea.

7. The plasma gasification method of claim 1, further comprising:
   removing slag from the arc plasma gasifier.

8. The plasma gasification method of claim 1, wherein the one or more feed materials further comprises plastic waste, wherein the at least one constituent gas comprises hydrogen gas and carbon monoxide, wherein the processing the at least one constituent gas further comprises:
   synthesizing methanol from at least a first portion of the carbon monoxide;
   converting at least a second portion of the carbon monoxide to carbon dioxide and additional hydrogen gas;
   capturing the carbon dioxide and the additional hydrogen gas; and
   feeding at least one portion of the hydrogen gas and at least one portion of the additional hydrogen gas into a fuel cell to produce electricity.

9. The plasma gasification method of claim 1, wherein the liquid feed stream of geothermal brine is untreated by a desalination process.

10. The plasma gasification method of claim 2, further comprising:
    controlling, by one or more artificial intelligence (AI) systems, operation of the arc plasma gasifier to maximize production of the hydrogen gas.

* * * * *